United States Patent
Tillotson (10) Patent No.: US 8,339,583 B2
(45) Date of Patent: Dec. 25, 2012

(54) VISUAL DETECTION OF CLEAR AIR TURBULENCE

(75) Inventor: Brian J. Tillotson, Kent, WA (US)

(73) Assignee: The Boeing Company, Chicago, IL (US)

( * ) Notice: Subject to any disclaimer, the term of this patent is extended or adjusted under 35 U.S.C. 154(b) by 672 days.

(21) Appl. No.: 12/505,182

(22) Filed: Jul. 17, 2009

(65) Prior Publication Data

US 2011/0013016 A1    Jan. 20, 2011

(51) Int. Cl.
*G01P 3/36* (2006.01)
*G01G 21/00* (2006.01)

(52) U.S. Cl. .................. 356/28; 701/472
(58) Field of Classification Search ........ 356/28; 455/431; 340/628; 701/472
See application file for complete search history.

(56) References Cited

U.S. PATENT DOCUMENTS

| | | | | |
|---|---|---|---|---|
| 3,696,670 A * | 10/1972 | Collis | ............. | 73/170.27 |
| 4,195,931 A * | 4/1980 | Hara | ............. | 356/454 |
| 4,266,130 A * | 5/1981 | Kuhn | ............. | 250/339.14 |
| 5,013,151 A * | 5/1991 | Hughes | ............. | 356/139.08 |
| 5,159,407 A * | 10/1992 | Churnside et al. | ............. | 356/499 |
| 5,343,287 A * | 8/1994 | Wilkins | ............. | 356/141.3 |
| 5,610,703 A * | 3/1997 | Raffel et al. | ............. | 356/28 |
| 5,831,570 A * | 11/1998 | Ammar et al. | ............. | 342/26 B |
| 6,208,937 B1 * | 3/2001 | Huddle | ............. | 701/472 |
| 6,366,854 B1 * | 4/2002 | Tsuchiya et al. | ............. | 701/468 |
| 6,480,142 B1 * | 11/2002 | Rubin | ............. | 342/26 R |
| 6,578,961 B2 * | 6/2003 | Vaez-Iravani | ............. | 356/237.2 |
| 6,590,520 B1 * | 7/2003 | Steele et al. | ............. | 342/26 R |
| 6,591,171 B1 * | 7/2003 | Ammar et al. | ............. | 701/16 |
| 6,828,923 B2 * | 12/2004 | Anderson | ............. | 340/968 |
| 6,903,752 B2 | 6/2005 | Ebersole et al. | | |
| 6,937,937 B1 * | 8/2005 | Manfred et al. | ............. | 702/2 |
| 7,343,793 B2 | 3/2008 | Tillotson et al. | | |
| 7,530,266 B2 | 5/2009 | Tillotson et al. | | |
| 7,592,955 B2 * | 9/2009 | Tillotson et al. | ............. | 342/378 |
| 7,705,879 B2 * | 4/2010 | Kerr et al. | ............. | 348/117 |
| 7,761,197 B2 * | 7/2010 | Puig | ............. | 701/14 |
| 7,859,419 B2 * | 12/2010 | Shen-Kuen et al. | ............. | 340/628 |
| 7,933,002 B2 * | 4/2011 | Halldorsson | ............. | 356/28 |

(Continued)

FOREIGN PATENT DOCUMENTS

DE    10010045 A1    9/2001

(Continued)

OTHER PUBLICATIONS

Raffel et al—Detecting Spatial density gradients around aircraft (—DE10010045A1—Sep. 13, 2001).pdf.*

(Continued)

*Primary Examiner* — Firmin Backer
*Assistant Examiner* — Michael A Chambers
(74) *Attorney, Agent, or Firm* — Farid Piroozmandi (57) ABSTRACT

Presented is a system and method for detecting clear air turbulence comprising an image capturing element, a lens having focal length adapted to focus a scene onto the image capturing element such that the combination of the lens and array of pixels are capable of optically resolving any visual distortions of features in the scene that are caused by turbulent air, and a processor. The processor compares the image with a subsequent image, or a stored image of the scene, to detect a change in refraction of light received from the feature in the scene that is due to turbulence and produces an indication of the area of turbulence in the scene.

28 Claims, 5 Drawing Sheets

U.S. PATENT DOCUMENTS

| | | | |
|---|---|---|---|
| 2003/0085890 A1* | 5/2003 | Baumberg et al. | 345/420 |
| 2004/0141170 A1* | 7/2004 | Jamieson et al. | 356/5.01 |
| 2006/0121893 A1* | 6/2006 | Tillotson et al. | 455/431 |
| 2008/0004533 A1* | 1/2008 | Jansen et al. | 600/476 |
| 2008/0043234 A1* | 2/2008 | Mirand et al. | 356/342 |
| 2008/0117419 A1* | 5/2008 | Hays et al. | 356/342 |
| 2008/0190192 A1* | 8/2008 | Bommier et al. | 73/170.11 |
| 2009/0009393 A1 | 1/2009 | Tillotson et al. | |
| 2009/0143988 A1 | 6/2009 | Tillotson | |
| 2009/0153555 A1* | 6/2009 | Herken et al. | 345/420 |
| 2009/0310118 A1* | 12/2009 | Halldorsson | 356/28 |
| 2010/0030401 A1* | 2/2010 | Rogers et al. | 701/3 |

FOREIGN PATENT DOCUMENTS

| | | |
|---|---|---|
| EP | 1422529 | 5/2004 |
| WO | 91/05269 | 4/1991 |
| WO | WO 9105269 A1 * | 4/1991 |
| WO | 2007/009759 A1 | 1/2007 |

OTHER PUBLICATIONS

Raffel et al,—Sep. 13, 2001), Detecting Spatial density gradients around aircraft—DE10010045A1.*

GB, Combined Search and Examination Report, Application No. GB1011937.8 (Sep. 20, 2010).

* cited by examiner

VISUAL DETECTION OF CLEAR AIR TURBULENCE

FIELD

Embodiments of the subject matter described herein relate generally to a method for estimating the magnitude and distance of turbulent pockets of air.

BACKGROUND

Airplane encounters with clear air turbulence at cruise altitude may produce serious injury. Clear air turbulence is difficult to forecast and even more difficult to detect with current methods. Clear air turbulence is turbulence that results where there are no clouds, precipitation, or visible particles such as dust in the air.

SUMMARY

Presented is a method and system for detecting clear air turbulence using a camera and associated software. The method and system detects small fluctuations in a visual scene that are caused by turbulence in the atmosphere, and measures the characteristics of these fluctuations to estimate the magnitude of the turbulence and the distance to the turbulence. The method and system reports an indication of the estimate of the turbulence to pilots of aircraft, allowing them to maneuver their aircraft to avoid the turbulence.

The features, functions, and advantages discussed can be achieved independently in various embodiments of the present invention or may be combined in yet other embodiments further details of which can be seen with reference to the following description and drawings.

BRIEF DESCRIPTION OF THE DRAWINGS

The accompanying figures depict various embodiments of the system and method of visual detection of clear air turbulence. A brief description of each figure is provided below. Elements with the same reference number in each figure indicated identical or functionally similar elements. Additionally, the left-most digit(s) of a reference number indicate the drawing in which the reference number first appears.

DETAILED DESCRIPTION

The following detailed description is merely illustrative in nature and is not intended to limit the embodiments of the invention or the application and uses of such embodiments. Furthermore, there is no intention to be bound by any expressed or implied theory presented in the preceding technical field, background, brief summary or the following detailed description.

Clear air turbulence is difficult to forecast and even more difficult to detect using current methods. Clear air turbulence is turbulence that results where there are no clouds, precipitation, or visible particles such as dust in the air. Pilots may learn of clear air turbulence from forecasts and other pilots that have recently flown through a pocket of turbulence. Generally, pilots turn on a "seat belt required" light and/or slow their aircraft's speed in anticipation of passing through suspected pockets of turbulence to reduce structural stresses on the aircraft and reduce discomfort to passengers. However, if the pilot is unaware of turbulence, the pilot may have little warning time to alert the passengers or otherwise change the configuration and velocity the aircraft.

A clear air turbulence system detects turbulence in the atmosphere and enables pilots maneuver their aircraft to avoid any turbulent pockets of air. In one embodiment, the clear air turbulence system warns the pilot of turbulence in the path of the aircraft. In another embodiment, the clear air turbulence system provides a visual navigational aid to enable a pilot to navigate around pockets of turbulent air. The clear air turbulence system may improve air safety, allowing airplanes to fly at cruise speeds with a reduced risk of running into unexpected turbulence that could damage the airplane or harm passengers. The clear air turbulence system also may increase the comfort of passengers in the airplane by allowing the pilot to navigate around pockets of turbulence or, if the turbulence is widespread, by allowing the pilot to slow the airplane and navigate through the least turbulence areas of the sky. Further, reducing the amount of turbulence that an airplane flies through over the airplane's useful life may also reduce the stresses on airframe and engine components that accrue during a lifetime of continuous operation. This will reduce component fatigue, permit safer long term operation of the aircraft, and reduce or shorten necessary maintenance cycles.

System Components and Operation

Figure 1:
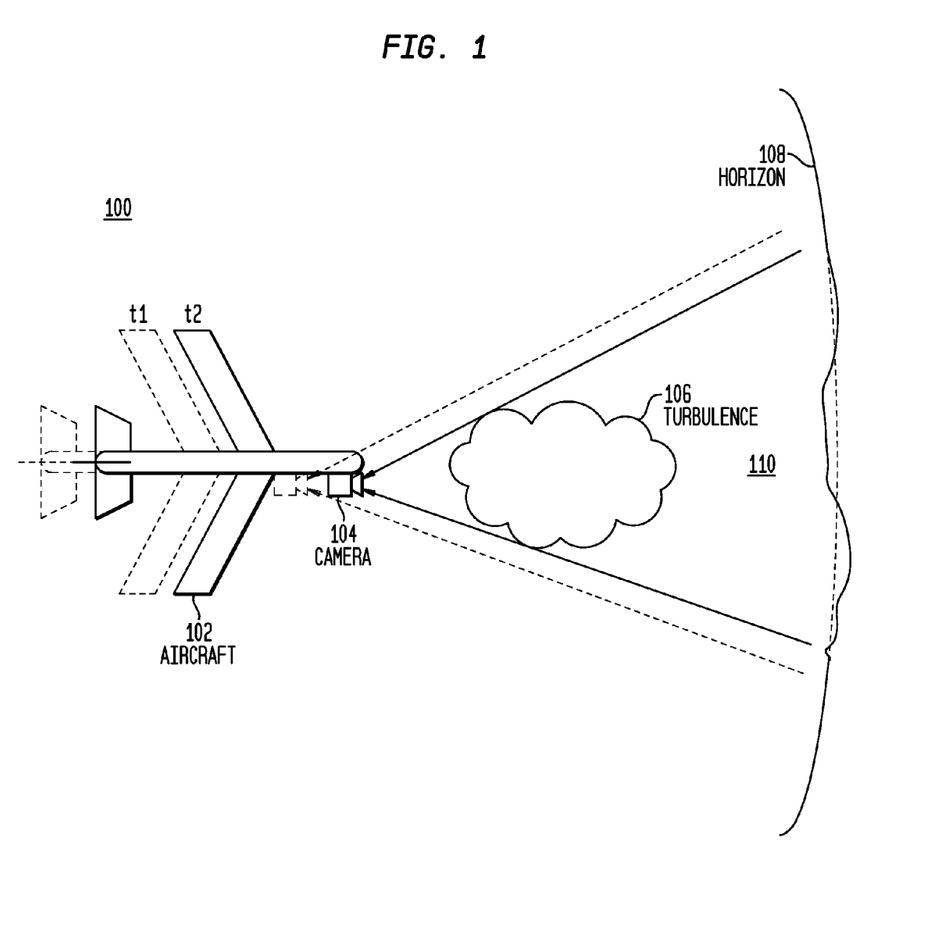
FIG. 1 is a diagram of an airplane detecting a patch of turbulence by analyzing distortions to the horizon in one embodiment of the clear air turbulence system and method.

Referring now to FIG. 1, the clear air turbulence system 100 comprises one or more cameras 104 mounted on or to an aircraft 102, and a computer for analyzing images from the cameras 104. The computer can be any suitable system capable of processing images, including but not limited to a PC or a customize circuitboard having a processor. The camera 104 is linked to the computer which receives the image from the camera 104. In an embodiment, the camera 104 uses a telephoto lens. In operation, the camera 104 is pointed approximately at the horizon 108, or an object having sufficient known detail, and a series of images or video is delivered to the computer. The camera 104 outputs digitized data of the image to the computer. In another embodiment, the computer digitizes an analog input from the camera 104 into digital images using a digital frame grabber.

Light returning to the camera 104 from the horizon 108 that passes through a pocket of turbulence 106 will be refracted differently than light passing through the rest of the sky. The difference in refraction is due to differences in humidity levels, temperatures, and/or pressures between the pocket of turbulence 106 and the surrounding ambient air. As a result of the difference in refraction, there will be distorted portions 110 of the horizon 108 where the horizon 108 appears shifted spatially and blurred.

Typically, the refractive bending of light by natural turbulence is usually less than 100 microradians and may therefore be too small to be detected by many cameras 104 using normal snapshot lenses. Therefore the camera 104 in the clear air turbulence system 100 uses a telephoto lens having a long focal length that magnifies the image and provides a suitable resolution for imaging by the camera 104. In an embodiment, the telephoto lens and the pixel resolution of the image capturing element, for example a CCD chip, are adapted to optically resolve at least 10 microradians of angle. For example, a telephoto lens having a 1-meter focal length can optically resolve approximately $10^{-5}$ radians when coupled with a one $cm^3$ CCD chip having one micron pixels arranged in a 1000× 1000 pixel matrix. In one embodiment, the telephoto lens is a zoom lens, capable of adjusting the magnification and therefore allowing the system operator to selectively trade off measurement accuracy for a wider field of view.

In an embodiment, the camera 104 includes a CCD having a very fine pitch, or a comparable image capturing means, is used to gather an image, either alone or in combination with a telephoto lens. In one embodiment, to maximize the resolution, the CCD is a monochrome CCD. Color CCDs generally use tiny filters arranged in a pattern over the CCD elements, which can cause unwanted image artifacts such as color changes near sharp edges of object depending upon how the light falls onto the CCD chip. Edge artifacts are unwanted image distortions that have to potential of being misinterpreted by the computer as turbulence. In other embodiments, the system uses a 3-CCD camera 104 which divides the image into three different CCDs, for example using birefringent materials, and therefore does not induce unwanted edge artifacts.

In embodiments, the camera 104 is a digital camera, a video camera, a high-resolution CCD camera, an HD camcorder. In embodiments, to enhance the image depth and dynamic range of the captured image, the camera 104 selectively uses filters, such as a polarization filter, a neutral density filter, or a red filter to avoid backscattered blue light. In embodiments, the camera 104 additionally is an infrared camera or selectively uses an image intensifier, such as a night vision tube, allowing the system to perform better in low light situations such as dusk or night time.

In an embodiment, the camera 104 is mounted on a rotatable swivel mount that allows the camera 104 to be rotated to view different portions of the sky. In an embodiment, the camera 104 is mounted on a multi-axis gimbal, allowing it to be angularly rotated in any direction. In these embodiments, the camera 104 may be rotated or oriented in order to scan a larger area. The output from the camera 104 is synchronized with an output from a rotational encoder or other similar orientation identifying means to correlate images from the camera 104 with the orientation of the camera. The motion of the camera 104 can be linked to the motion of the aircraft 102, for example through a navigation unit such as a GPS receiver, an inertial measurement unit or IMU, or both. The IMU measures changes in camera orientation due to rotation or twisting of the aircraft 102 and can be used to maintain orientation of the camera towards a desired point in the sky. In an embodiment, the motion and orientation of the camera 104 can be measured by changes in the positions of visual features in a sequence of images, and said motion and orientation measurements can be used to digitally align, or register, images to each other as if the camera 104 were stationary. In an embodiment, the camera 104 is substantially fixed and a rotatable mirror is used to change the direction of viewing of the camera 104. In an embodiment, the mirror is a first surface mirror for better clarity. In an embodiment, the camera 104 is mounted in a vibration reducing mount. In an embodiment, the camera 104 is gyroscopically stabilized.

Image Transformations and Scene Registration

Figure 5:
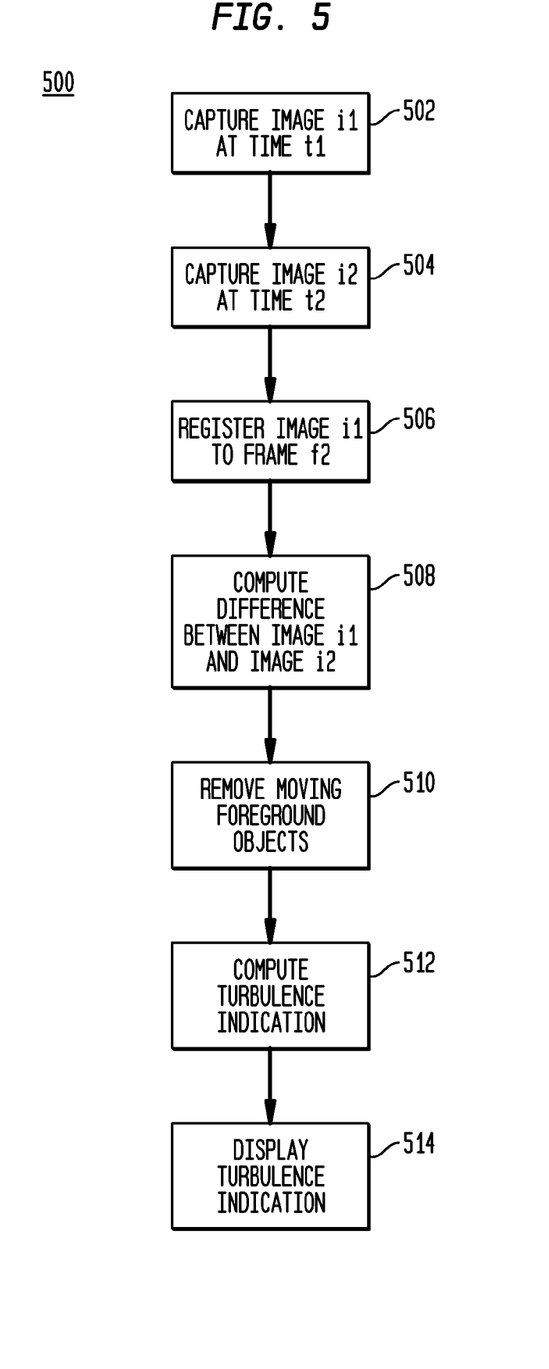
FIG. 5 is a flow chart illustrated process steps in one embodiment of the clear air turbulence system and method.

Referring now to FIGS. 1 and 5, the aircraft 102 in flight moves from a first position at time t1 to a second position at time t2. While the aircraft 102 is moving, the camera 104 takes images of a scene having a feature, for example the horizon 108. The computer captures the scene on the camera 104 into a series of images, for example by capturing 502 a first image i1 at time t1, and capturing 504 a second image i2 at time t2, where t2>t1. Typically, t2<t1+1 second, however in embodiments the interval between t2 and t1 can be any suitably short interval of time. An image is generally made up of an ordered matrix of pixels, for example a 12 megapixel image having a 4:3 ratio comprises a rectangular image having 4000 pixels along one axis and 3000 pixels along a second axis.

In clear air, when no turbulence 106 is present, the images will blend smoothly with each next image, with simple geometric transformations known to person skilled in the art. When turbulence 106 is present, however, some parts of the image will appear distorted, for example the distorted portions 110 of the horizon as illustrated in FIG. 1. The distortion portions 110 will vary from image to image, whereas the rest of the horizon 108 will not vary significantly from image to image.

In a comparison between a two image, for example image i1 at time t1 and image i2 at time t2, features such as the horizon 108 in one image can be easily registered with similar features in another image using simple geometric transformations. In one embodiment, the computer performs a transformation of a first image i1 at time t1 into a predicted subsequent image, and compares the predicted subsequent image with the actual subsequent image at time t2. In another embodiment, the computer performs a similar process but transforms the second image into a predicted first image. However, transforming the second image has the disadvantage that the system must wait until the second image is received by the computer before performing the transformation, creating a possible time lag.

In another embodiment, both a first image and a second image are transformed to a internal standard image format used by the computer before being compared. This embodiment has the advantage that each image is transformed independently of any camera 104 related artifacts of the other image and simplifying computations. For example, using an internal standard image, each image can be different in terms of angle, rotation, zooming, and aperture and then mapped to the angle, rotation, zoom level and aperture of the internal standard image. Further, using the internal standard image simplifies comparing image from different cameras 104, which may have different focal lengths or may look at the same scene from different angles, for example if two cameras 104 are mounted on opposite wingtips.

Depending upon the motion of the aircraft 102, the geometric transformation may be a translation operation, a scaling operation, a rotation operation, or a projection operation to one or both of the scenes captured in the images. To perform the transformation, the computer first estimates the distance of features in the scene. For example, if the camera 104 is facing towards the horizon 108, the distance to the horizon 108 is a simple monotonic function of the altitude of the aircraft 102. The computer performs an estimate of the motion of the aircraft 102 including groundspeed and direction, for example by using the movement of ground features in the image. Once the computer has the distance estimates for features in the images, the computer uses the distance estimate and along with the time, t1 and t2, between the images and motion information from the airplane to determine the appropriate transformation to perform to one or both images. The computer registers 506 the images by adjusting the size, position, and/or orientation of one or both of the images, for example by registering 506 image i1 to image i2. In this example, image i1 is digitally translated, scaled, rotated, and/or projected so that features in image i1 are aligned with matching features in image i2, which is also called scene registration.

In an embodiment, the clear air turbulence system 100 determines the position of the aircraft 102 by comparing images of the ground with information from a geographic information system, or GIS, having a database of visual terrain characteristics. In another embodiment, the clear air turbulence system 100 determines the position of the aircraft 102 using GPS. In these embodiments, distance measurements for transforming or registering 506 an image, or even individual features within a image, can be computed with improved accuracy. In one embodiment of the clear air turbulence system 100 comprising both a GIS interface and a GPS position interface, the clear air turbulence system 100 performs scene registration of images using particular portions or features within the images.

After the registration 506 of image i1 is performed, the clear air turbulence system 100 computes the difference 508 between registered image i1 and image i2. In one embodiment, computing the difference 508 between registered image i1 and image i2 comprises subtracting the pixels of registered image i1 from image i2, and is therefore a simple difference image. In embodiments, image i1 and image i2 are compared using any methodology that produces a usable difference result, including but not limited to using one or more convolution matrixes with matrix terms that would be known to one of skill in the art.

When there is a difference between registered image i1 and image i2, that difference indicates changes that are unrelated to motion of the camera 104. The changes may be due to the motion of objects in the scene, for example a moving vehicle, or due to turbulent refraction of light travelling from features in the scene to the camera 104. In one embodiment, the clear air turbulence system 100 also performs the additional step of removing 510 foreground objects from the difference image, such as moving objects on the ground, clouds, or other aircraft in the sky.

Figure 3:
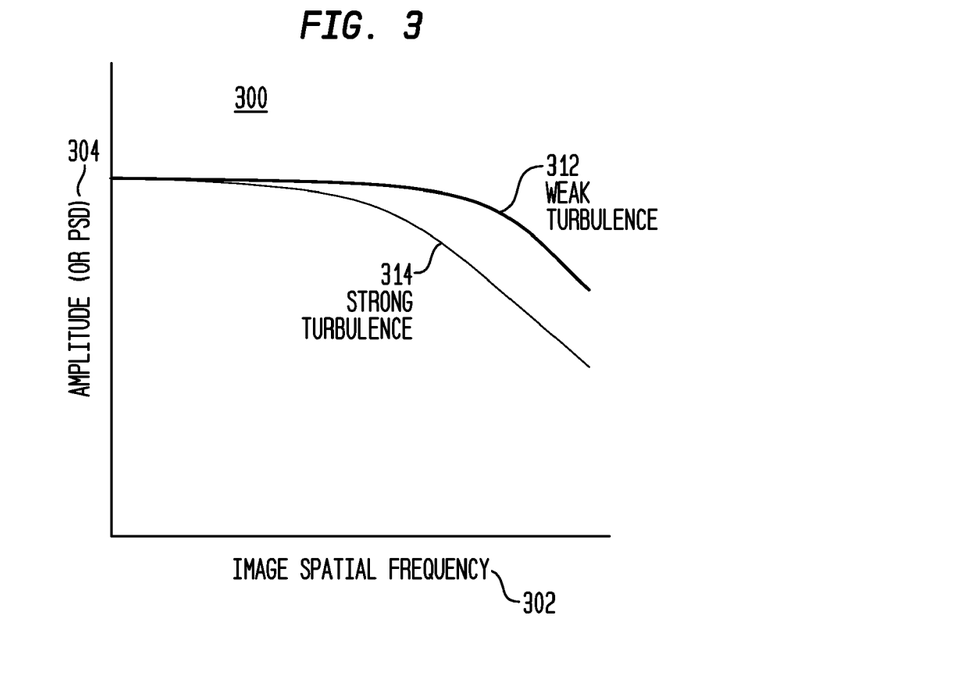
FIG. 3 is a graph illustrating the decrease in high frequency spectral content of an image due to the blurring of background features caused by refraction through different densities of turbulent air in one embodiment of the clear air turbulence system and method.

From one or more difference images, the clear air turbulence system 100 computes 512 a turbulence indication. When there is little turbulence 106, the difference image will contain little or no information. Difference images having information indicate a distortion or scintillation caused by the turbulence 106. In an embodiment, to compute 512 a turbulence indication, the computer calculates a power spectral density, PSD, of a feature of an image at various angular scales. Referring now to FIG. 3, a graph illustrates the spectral content 300 of two images of the same scene, one image taken through a pocket of strong turbulence 314, and a second image of the same scene taken through air where there is only weak turbulence 312. The graph illustrates that the amplitude 304 for a range of spatial frequencies 302 of the image taken through strong turbulence shows a larger drop in higher frequency content than the image taken through weak turbulence 312. The drop in higher spatial frequency contents corresponds to the blurring of edges in the image due caused by the increase amount of turbulence 106 and the increase amount of refractive distortion.

Figure 4:
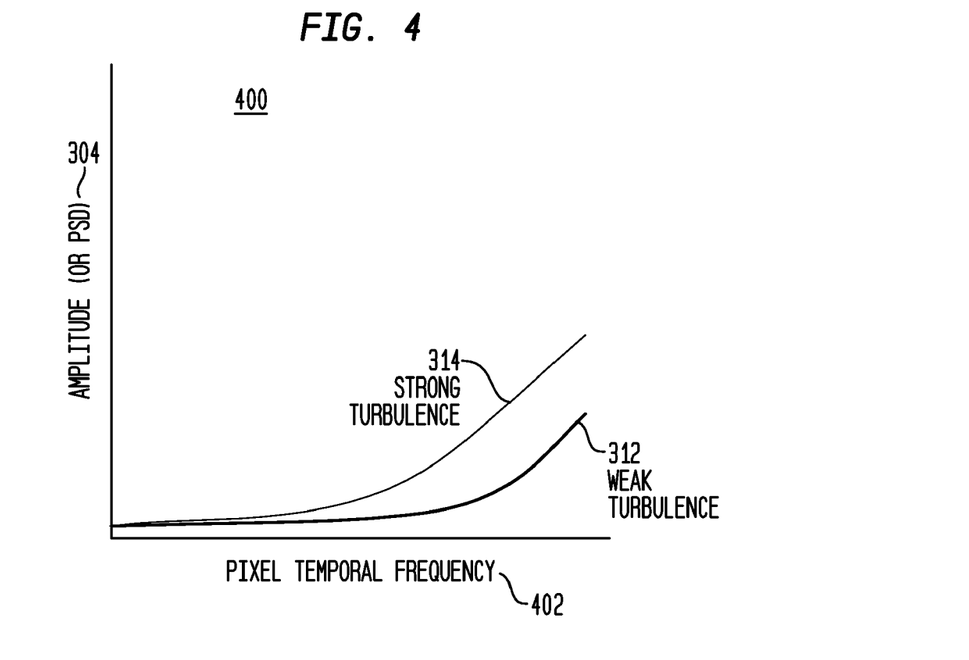
FIG. 4 is a graph illustrating the increase in high frequency spatial content of a scene as measured across multiple successive images due to movement and scintillation of background features in successive images due to dynamic changes in refraction cause by changing densities in turbulent air in one embodiment of the clear air turbulence system and method.

Because the distortion or scintillation vary over time, in embodiments the clear air turbulence system 100 also calculates changes to the difference images using various temporal scales to compute 512 the turbulence indication. These temporal changes are used to determine the severity and/or dynamically changing characteristics of the turbulence 106. In an embodiment, to compute 512 a turbulence indication, the computer calculates a power spectral density, PSD, of a feature in a set of images at various temporal scales. Referring now to FIG. 4, a graph illustrates the change in temporal frequency 400 for pixels of multiple images of the same scene, one set of images taken through a pocket of strong turbulence 314, and a second set of images of the same scene taken through air where there is only weak turbulence 312. The graph illustrates that there is a higher spectral content in the set of images taken through a pocket of strong turbulence 314 than the set of images taken through weak turbulence. This measurable increase results from the small displacements of features and flickering caused by the increased amount of refractive distortion due to turbulence 106. In embodiments, the clear air turbulence system 100 uses Fourier transforms, multi-scale correlation between images, measure of information entropy or other parameters to reveal angular blurring or temporal flickering.

Figure 2:
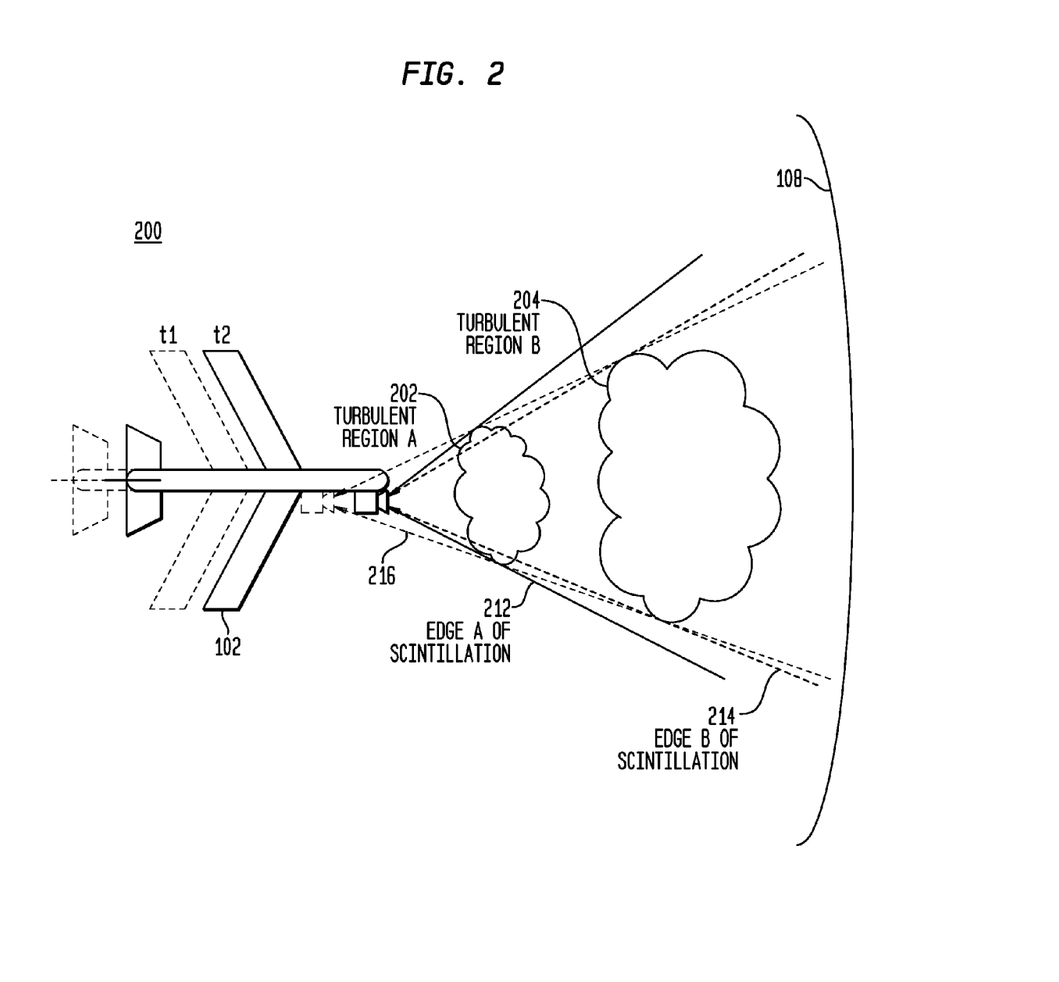
FIG. 2 is a diagram illustrating how to detect the range to, and size of, a patch of turbulence by analyzing the angular rate of change of a patch of scintillation in one embodiment of the clear air turbulence system and method.

To determine the range to the turbulence 106, the clear air turbulence system 100 uses the rate of change of the size of the pocket of turbulence 106. Referring now to FIG. 2, a small turbulent region 202, turbulent region A, initially appears similar to a larger turbulent region 204, turbulent region B. This is because both turbulent regions 202, 204 have initially similar angular extents 216 as illustrated by dotted line. However, as the aircraft 102 moves from the first position at time t1 to a second position at time t2, turbulent region A's angular extent 212, illustrated by the solid line, will grow faster than turbulent region B's angular extent 214, illustrated by the dashed line. The rate of change of the angular extent 212, 214 is used to compute the distance to the turbulent region 202, 204. Therefore, by tracking the size of a patch of scintillation through successive images and measuring the growth of the angular extent 212, 214, the clear air turbulence system 100 can determine both an estimated range to the turbulent region 202, 204 and an estimated size.

In another embodiment, the camera 104 is facing sideways, perpendicular to the moving aircraft 102. In this embodiment, the distance to the turbulence 106 is less than the distance to the horizon 108. Patches of scintillation will move across the scene in fewer successive images than features on the horizon or objects on the ground behind the turbulence 106. The turbulence will have a higher angular velocity relative to the background features that are far from the aircraft. Therefore, by tracking the angular momentum of a patch of scintillation through successive images, the clear air turbulence system 100 can determine an estimated range to the turbulence 106. Using a combination of the forward looking camera 104 embodiment and the sideways facing camera 104 embodiment the clear air turbulence system 100 can detect turbulence 106 at various ranges and angles to the aircraft 102.

Figure 6:
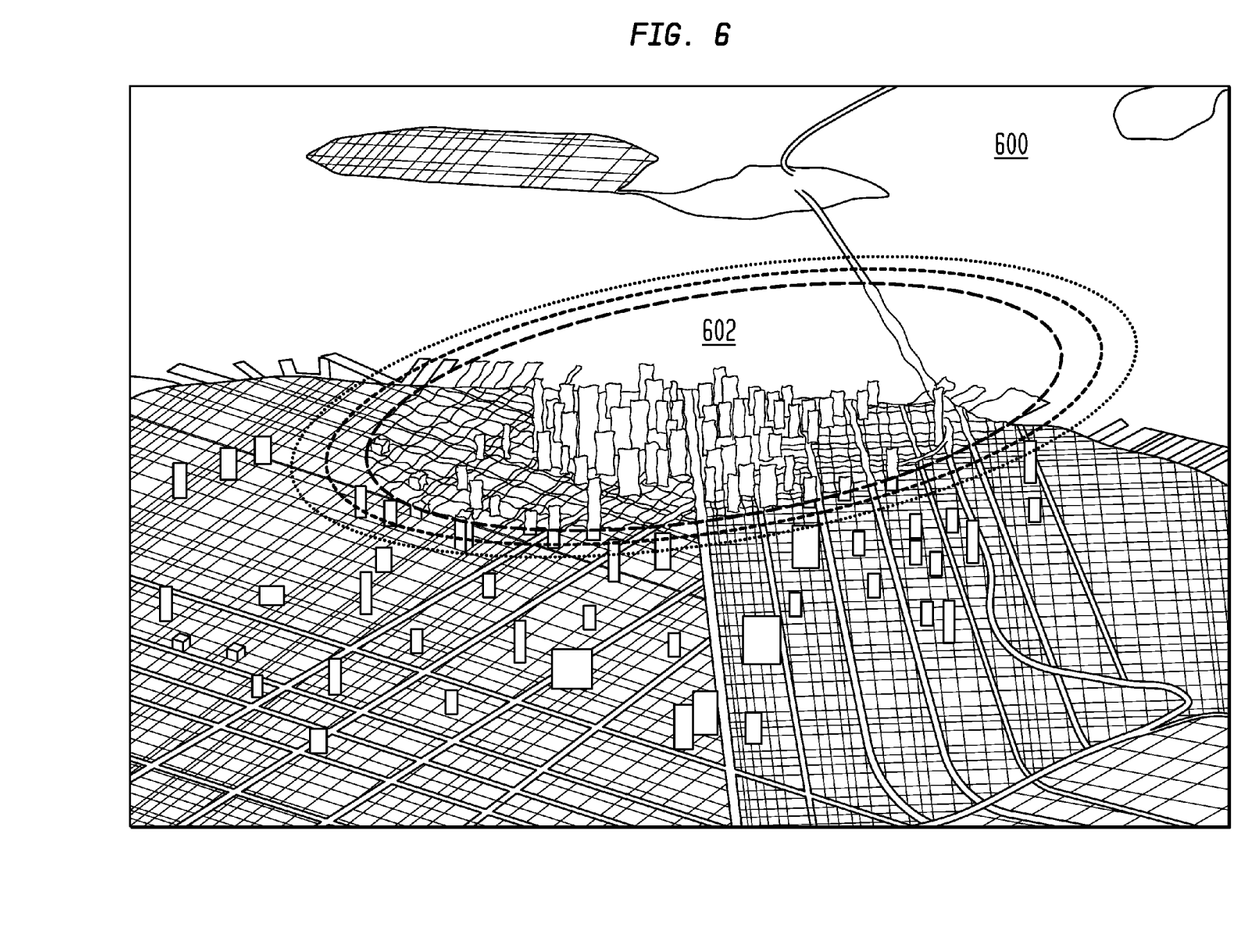
FIG. 6 in an exemplary screen shot of a background image overlaid with a graphic showing isobars representing turbulence in one embodiment of the clear air turbulence system and method.

Referring to FIG. 6, in an embodiment, distances to city skylines or even particular building features provide additional information about atmospheric distortions due to turbulence 106. Using information from a GIS, the clear air turbulence system 100 estimates the contrast and spatial information content of a background scene. Urban and suburban neighborhoods often have high contrast and a high amount of spatial detail, for example buildings with regularly spaced windows provide information about turbulent air between the camera 104 and the buildings. Rural areas typically have less contrast and less spatial detail. GIS information allows the clear air turbulence system 100 to choose an appropriate threshold PSD for determining whether or not to report a turbulence indication. When over deserts or water, there is generally an absence of high spatial frequency components that is unrelated to turbulence. The clear air turbulence system 100 provides a warning to pilots when the background is insufficient to support effective turbulence detection.

The clear air turbulence system 100 displays the turbulence indication to the pilot of the aircraft 102. In embodiments, the turbulence indication an audible warning alarm, a graphical representation of the turbulence, an input to an autopilot navigation system, and/or a broadcasted electronic message. In one embodiment shown in FIG. 6, the turbulence indication is used to overlay a warning graphic on top of a real time image of the air 600 in front of the aircraft 102, for example using isobars 602 as shown in FIG. 6. In embodiments, the clear air turbulence system 100 overlays color shading or flashes an overlaid graphics that can be used to similarly warn pilots of turbulence 106. In an embodiment, the clear air turbulence system 100 performs additional processing and provides a probability indication of turbulence 106 in addition to other warnings. In an embodiment, the clear air turbulence system 100 continuously displays the amount of computed 512 turbulence 106, for example in the form of a heads up display for the pilot, allowing the pilot to draw her own conclusions about the presence and magnitude of turbulence 106 the aircraft 102 is approaching. In another embodiment, the clear air turbulence system 100 only displays warning graphics or issues warning messages once a threshold PSD is crossed, allowing pilots to focus on other tasks.

In an embodiment, the clear air turbulence system 100 sends the turbulence indication to a weather forecasting center. In an embodiment, the clear air turbulence system 100 shares the turbulence indication with other nearby aircraft or systems on the ground. In an embodiment, the clear air turbulence system 100 shares raw or interpreted visual data with nearby aircraft to develop a better indication of local turbulence 106. In an embodiment, the data is shared via military communications links, for example Link-16. In an embodiment, the turbulence indication is shared as a track of an airborne object.

The embodiments of the invention shown in the drawings and described above are exemplary of numerous embodiments that may be made within the scope of the appended claims. It is contemplated that numerous other configurations of the clear air turbulence system 100 may be created taking advantage of the disclosed approach. It is the applicant's intention that the scope of the patent issuing herefrom will be limited only by the scope of the appended claims.

What is claimed is:

1. A clear air turbulence detection system, comprising:
   an image capturing element configured to capture an ambient light image of a scene;
   a lens having a focal length adapted to focus said scene onto said image capturing element such that a combination of said lens and said image capturing element is adapted to optically resolve a visual distortion of a feature in said scene due to turbulence; and
   a processor adapted to process said image of said scene from said image capturing element, said processor being adapted to compare a plurality of said images, captured at pre-set time intervals, to detect a non-uniform change in refraction of light received from said feature from one of said plurality of said images to a next successive one of said plurality of images due to turbulence and produce an indication of an area of turbulence.

2. The clear air turbulence detection system of claim 1, wherein said image capturing element is a CCD camera.

3. The clear air turbulence detection system of claim 1, wherein said lens is a telephoto lens.

4. The clear air turbulence detection system of claim 1, wherein said combination of said lens and said image capturing element is adapted to have a minimum resolving capability of between approximately 10 microradians of angle and approximately 100 microradians of angle.

5. The clear air turbulence detection system of claim 1, wherein the clear air turbulence system is mounted on a moving platform and wherein said processor is further adapted to transform scene in a first one of said images relative to said scene in a second, successive one of said images such that a feature in said first one of said images approximates a position, a size and an orientation of said feature in said second one of said images.

6. The clear air turbulence detection system of claim 5, wherein said processor is adapted to transform said scene in said first one of said images using a transformation selected from the group consisting of translating said scene, scaling said scene, rotating said scene, and projecting said scene.

7. The clear air turbulence detection system of claim 5, further comprising:
   an inertial navigation device providing an orientation data of said feature; and
   global positioning system data providing a position of said moving platform, and wherein said processor is adapted to process said global positioning system data and said orientation data to query a geographic information system source for image data of said feature, and
   wherein said processor is adapted to compare an image of said feature captured by said image capturing element with said image data of said feature from said geographic information system source to detect a change in spatial information content of said feature due to an area of turbulence.

8. The clear air turbulence detection system of claim 1, wherein said processor detects said change in refraction of said feature due to an area of turbulence by performing a power spectral density operation selected from the group consisting of measuring a decrease in a high spatial frequency content of a measured power spectral density of a feature of an image compared with a calculated power spectral density of said feature of said image, and an increase in a high frequency content of a measured temporal power spectral density of a feature over a plurality of images compared with a calculated power spectral density of said feature over said plurality of images.

9. The clear air turbulence detection system of claim 1, wherein said processor detects turbulence by detecting angular blurring in an image.

10. The clear air turbulence detection system of claim 1, wherein said processor detects turbulence by detecting temporal flickering between images.

11. The clear air turbulence detection system of claim 1, wherein said processor detects a range to said turbulence by tracking a size of an area of scintillation through a plurality of images to determine a rate of change in an angular extent of said area of scintillation.

12. The clear air turbulence detection system of claim 1, wherein said turbulence indication is selected from the group consisting of an audible alarm, a graphical display of said turbulence, a graphical overlay superimposed on a real-time image, an input to an autopilot navigation system, and a broadcasted electronic message.

13. A method of detecting clear air turbulence, comprising:
capturing a first image of a scene illuminated by ambient light;
capturing a second image, at a pre-set time interval subsequent to capturing said first image, consisting essentially of said scene illuminated by ambient light;
selecting a feature present in said first image and said second image;
registering said first image to said second image such that said feature in said first image has approximately a same position, scale, and orientation as said feature in said second image;
comparing said feature in said first image with said feature in said second image to determine a non-uniform change to a portion of said feature between said first image and said second image; and
displaying a turbulence indication if said non-uniform change to said feature is present above a pre-set threshold.

14. The method of detecting clear air turbulence of claim 13, wherein said first image and second image are adapted to resolve a minimum angular resolution of approximately 10 microradians to approximately 100 microradians.

15. The method of detecting clear air turbulence of claim 13, further comprising:
removing a change to a portion of said feature caused by moving objects.

16. The method of detecting clear air turbulence of claim 13, further comprising:
detecting an angular blurring in an image; and
displaying a turbulence indication base upon said angular blurring.

17. The method of detecting clear air turbulence of claim 13, further comprising:
detecting a temporal flickering in a set of images; and
displaying a turbulence indication base upon said temporal flickering.

18. The method of detecting clear air turbulence of claim 13, wherein said change to a portion of said feature is an increase in a high temporal frequency content of a power spectrum distribution of said feature.

19. The method of detecting clear air turbulence of claim 13, further comprising:
computing a power spectral density of said feature of said second image;
computing a power spectral density of said feature of said first image; and
comparing said power spectral density of a said first image and said second image to determine said turbulence indication.

20. The method of detecting clear air turbulence of claim 13, further comprising:
receiving an orientation data of said orientation of said scene of said first image relative to said feature;
receiving a position data of a distance to said feature of said first image; and
transforming said scene of said second image to have approximately a same position, scale, and orientation as said feature in said first image.

21. The method of detecting clear air turbulence of claim 20, further comprising:
querying a geographic information service for a data correlating to said feature; and
computing said feature of said second image from the data of said geographic information service.

22. The method of detecting clear air turbulence of claim 13, wherein said displaying a turbulence indication is selected from the group consisting of playing an audible alarm, displaying a graphical display of said turbulence, superimposing a graphical overlay on a real-time image, sending a message to an autopilot navigation system, and broadcasting an electronic message.

23. An aircraft with a turbulence detection system, comprising:
a turbulence detection system having a camera system and an image processing system;
said camera system being configured to capture an ambient light image of a scene;
said image processing system including a processor adapted to process said image of said ambient light image of said scene by comparing a plurality of said ambient light images of said scene, captured at pre-set time intervals, to detect a non-uniform change in refraction of ambient light received from said scene from one of said plurality of said images to a next successive one of said plurality of said images due to turbulence, and produce an indication of an area of turbulence;
an aircraft adapted to mount said camera system; and
a turbulence alerting system in a cockpit of said aircraft, said turbulence alerting system being in electronic communication with said image processing system.

24. The aircraft of claim 23, wherein said camera system further comprises: a CCD camera having a pixel size and focal length adapted to resolve visual distortions in a scene imaged by said CCD camera that are caused by turbulent air.

25. The aircraft of claim 23, wherein said image processing system is adapted to select a selected image from said plurality of images, to select a reference image with which to compare said selected image, to perform a geometric image transformation selected from the group consisting of translating a scene, scaling a scene, rotating a scene, and projecting a scene, said geometric image transformation registering scenes from two different perspectives with one another, and to compare said selected image to said reference image to produce said indication of turbulence.

26. The aircraft of claim 25, wherein said reference image is selected from the group consisting of a second selected image from said plurality of images, a previously stored image of the scene, an image of the scene from a geographic information system, and an image of a feature in the scene from a geographic information system.

27. The aircraft of claim 23, wherein said image processing system detects a change selected from the group consisting of an angular blurring of a feature in an image, a temporal flickering of a feature in a set of images, a change in size of an area of scintillation of a feature in an image, a change in high temporal frequency content of a feature in an image, and a change in power spectral density of a feature in an image.

28. The aircraft of claim 23, wherein said turbulence alerting system receives said indication of turbulence from said image processing system, and said turbulence alerting system is selected from the group consisting of an audible alarm, a graphical display of said turbulence, a graphical overlay superimposed on a real-time image, an input to an autopilot navigation system, and a broadcasted electronic message.

* * * * *